(12) United States Patent
Naya et al.

(10) Patent No.: US 9,304,086 B2
(45) Date of Patent: Apr. 5, 2016

(54) RAMAN SPECTROMETRY METHOD AND RAMAN SPECTROMETRY APPARATUS

(71) Applicant: FUJIFILM Corporation, Tokyo (JP)

(72) Inventors: Masayuki Naya, Ashigarakami-gun (JP); Shogo Yamazoe, Ashigarakami-gun (JP)

(73) Assignee: FUJIFILM Corporation, Tokyo (JP)

(*) Notice: Subject to any disclaimer, the term of this patent is extended or adjusted under 35 U.S.C. 154(b) by 92 days.

(21) Appl. No.: 14/081,294

(22) Filed: Nov. 15, 2013

(65) Prior Publication Data

US 2014/0071447 A1 Mar. 13, 2014

Related U.S. Application Data

(63) Continuation of application No. PCT/JP2012/003153, filed on May 15, 2012.

(30) Foreign Application Priority Data

May 17, 2011 (JP) ................................. 2011-110410

(51) Int. Cl.
*G01N 21/65* (2006.01)

(52) U.S. Cl.
CPC .............. *G01N 21/65* (2013.01); *G01N 21/658* (2013.01)

(58) Field of Classification Search
CPC ... G01N 21/65; G01N 21/658; G01N 21/554; G01N 21/648
See application file for complete search history.

(56) References Cited

U.S. PATENT DOCUMENTS

| 7,787,117 B1* | 8/2010 | Leona et al. ................... 356/301 |
| 2004/0161369 A1 | 8/2004 | Chan et al. |
| 2007/0217003 A1* | 9/2007 | May ..................... G02B 5/0221 359/454 |
| 2008/0080816 A1* | 4/2008 | D'Urso et al. .................. 385/77 |
| 2008/0137081 A1 | 6/2008 | Murakami |

(Continued)

FOREIGN PATENT DOCUMENTS

| JP | 6-34530 A | 2/1994 |
| JP | 2002-257721 A | 9/2002 |
| JP | 2002257721 | * 9/2002 |

(Continued)

OTHER PUBLICATIONS

Ghadarghadr, S. et al. "Plasmonic array nanoantennas on layered substrates: modeling and radiation characteristics," Optics Express, 2009, vol. 17, No. 21, p. 18556.

(Continued)

*Primary Examiner* — Michael A Lyons
*Assistant Examiner* — Dominic J Bologna
(74) *Attorney, Agent, or Firm* — Birch, Stewart, Kolasch & Birch, LLP

(57) ABSTRACT

A surface enhanced Raman spectrometry apparatus is constituted by: a transparent substrate; a metal member that causes surface enhanced Raman scattering to occur, formed on a surface of the transparent substrate; a pressing mechanism that presses a sample placed in contact with the metal member against the metal member; a measuring light irradiating optical system that irradiates a measuring light beam onto the sample through the transparent substrate; and a light detecting section that spectrally detects Raman scattered light, which is generated when the measuring light beam is irradiated onto the sample, through the transparent substrate.

11 Claims, 3 Drawing Sheets

(56) References Cited

U.S. PATENT DOCUMENTS

2009/0237647 A1* 9/2009 Azimi et al. ............... 356/51
2014/0016127 A1* 1/2014 Yamazoe ............... B82Y 20/00
356/301

FOREIGN PATENT DOCUMENTS

| JP | 2003-28802 A | 1/2003 |
| JP | 2005-233637 A | 9/2005 |
| JP | 2006-514286 A | 4/2006 |
| JP | 2008-164584 A | 7/2008 |

OTHER PUBLICATIONS

International Search Report issued in PCT/JP2012/003153 mailed Sep. 18, 2012.

Wang, H. et al. "Nanosphere Arrays with Controlled Sub-10-nm Gaps as Surface-Enhanced Raman Spectroscopy Substrates," J. Am. Chem. Soc., 2005, vol. 127, pp. 14992-14993.

Written Opinion of the International Searching Authority issued in PCT/JP2012/003153 mailed Sep. 18, 2012.

Chinese Office Action issued Apr. 3, 2015 in corresponding Chinese Application No. 201280023630 with an English Translation.

Japanese Office Action and English translation thereof, dated Jan. 27, 2015, for Japanese Application No. 2011-110410.

Chinese Office Action issued Sep. 14, 2015 in corresponding Chinese Application No. 201280023630.X with an English Translation.

J. Y. Yang et al., "Surface-Enhanced Raman Scattering Active Substrates", IEEE Nanotechnology Magazine, vol. 5, No. 1, pp. 12-16, 2011.

* cited by examiner

RAMAN SPECTROMETRY METHOD AND RAMAN SPECTROMETRY APPARATUS

CROSS-REFERENCE TO RELATED APPLICATIONS

This application is a Continuation of PCT International Application No. PCT/JP2012/003153 filed on May 15, 2012, which claims priority to Patent Application No. 2011-110410 filed in Japan on May 17, 2011, all of which are hereby expressly incorporated by reference into the present application.

TECHNICAL FIELD

The present invention is related to a Raman spectrometry apparatus. More particularly, the present invention is related to a surface enhanced Raman spectrometry apparatus that amplifies Raman scattered light with a metal member and detects the amplified Raman scattered light.

The present invention is also related to a surface enhanced Raman spectrometry method that utilizes such a Raman spectrometry apparatus.

BACKGROUND ART

Raman spectrometry, which identifies and detects substances included in samples by applying the Raman effect, is conventionally known. The Raman effect is a phenomenon in which light having a wavelength different from that of incident light is scattered when the incident light is caused to enter a substance. The difference in energy, that is, the difference in wavelengths, between the scattered light (Raman scattered light) and the incident light corresponds to the molecular structure or the crystal structure of the substance. Raman spectrometry utilizes this phenomenon, by irradiating a light beam having a single wavelength onto a sample, spectrally detecting Raman scattered light generated thereby, and identifying specific substances.

Recently, surface enhanced Raman spectrometry (SERS: Surface Enhanced Raman Scattering), which is capable of significantly amplifying Raman scattered light and detects the amplified Raman scattered light, has been proposed and is being widely researched. Surface enhanced Raman spectrometry utilizes the fact that the intensity of Raman scattered light is amplified when light is irradiated onto a substance which is in contact with a metal member having fine protrusions and recesses on the surface thereof, and enables detection of extremely small amounts of substances. PCT Japanese Publication No. 2006-514286, Japanese Unexamined Patent Publication No. 2008-164584, and S. Ghadarghadr et al., "Plasmonic array nanoantennas on layered substrates: modeling and radiation characteristics", OPTICS EXPRESS, Vol. 17, No. 21, p. 18556, 2009 disclose examples of apparatuses for performing surface enhanced Raman spectrometry.

SUMMARY OF THE INVENTION

Conventional surface enhanced Raman spectrometry apparatuses disclosed in PCT Japanese Publication No. 2006-514286 and the like are configured such that a measuring light beam is irradiated onto a sample in contact with a metal member formed on the surface of a substrate from the side of the substrate on which the metal member is formed, and Raman scattered light generated at this time is detected at the side from which the measuring light beam is irradiated. For this reason, it had been extremely difficult to directly spectrally analyze opaque samples, such as samples which are delivered on filter paper by paper chromatography pieces of living tissue, using conventional surface enhanced Raman spectrometry apparatuses.

The present invention has been developed in view of the foregoing circumstances. It is an object of the present invention to provide a surface enhanced Raman spectrometry apparatus and a surface enhanced Raman spectrometry method capable of facilitating measurements of opaque samples.

A surface enhanced Raman spectrometry apparatus according to the present invention comprises:

a transparent substrate;

a metal member that causes surface enhanced Raman scattering to occur, formed on a surface of the transparent substrate;

a pressing mechanism that presses a sample placed in contact with the metal member against the metal member;

a measuring light irradiating optical system that irradiates a measuring light beam onto the sample through the transparent substrate; and a light detecting means for spectrally detecting Raman scattered light, which is generated when the measuring light beam is irradiated onto the sample, through the transparent substrate.

Note that the sample may be a sample (particularly a solid sample) itself as the target of measurement, or a liquid sample which is delivered to a liquid permeable substance such as filter paper.

It is particularly desirable for the surface enhanced Raman spectrometry apparatus of the present invention to further comprise:

a positioning member that maintains the transparent substrate at a predetermined position against a pressing force applied by the pressing mechanism.

The pressing mechanism comprising a plate shaped member that contacts the sample and a spring means for urging the plate shaped member toward the metal member may be favorably employed.

It is desirable for the metal member to have a structure of protrusions and recesses in which the sizes of the protrusions and recesses is smaller than the wavelength of the measuring light beam.

It is desirable for the main component of the metal member to be at least one metal selected from a group consisting of: Au, Ag, Cu, Al, Pt, Ni, Ti, and alloys thereof.

Meanwhile, a surface enhanced Raman spectrometry method of the present invention is that which performs Raman spectrometry using a surface enhanced Raman spectrometry apparatus of the present invention.

In the surface enhanced Raman spectrometry method of the present invention, a liquid permeable substance such as filter paper impregnated with a liquid sample may be employed as the sample.

In the case that a liquid permeable substance impregnated with a liquid sample is employed, it is desirable for a configuration to be adopted, wherein:

liquid samples are impregnated into each of a plurality of locations of the liquid permeable substance;

the measuring light beam is individually irradiated on each of the plurality of locations; and Raman scattered light generated by each irradiating operation is detected.

It is desirable for the liquid samples impregnated into each of the plurality of locations to be separated from each other by chromatography.

Alternatively, a solid sample itself such as a piece of living tissue may be employed as the sample. In the case that the solid sample itself is employed as well, it is desirable for the measuring light beam to be individually irradiated onto each a plurality of locations of the solid sample, and for Raman scattered light generated by each irradiating operation to be detected.

The surface enhanced Raman spectrometry apparatus of the present invention comprises: the transparent substrate; the metal member that causes surface enhanced Raman scattering to occur, formed on a surface of the transparent substrate; the pressing mechanism that presses a sample placed in contact with the metal member against the metal member; the measuring light irradiating optical system that irradiates a measuring light beam onto the sample through the transparent substrate; and the light detecting means for spectrally detecting Raman scattered light, which is generated when the measuring light beam is irradiated onto the sample, through the transparent substrate. Therefore, the measuring light beam can be irradiated onto opaque samples through the transparent substrate. In addition, Raman scattered light generated when the measuring light beam is irradiated onto samples can be spectrally detected through the transparent substrate. Therefore, surface enhanced Raman spectrometry can be simply executed even on opaque samples.

The surface enhanced Raman spectrometry method of the present invention performs Raman spectrometry employing the surface enhanced Raman spectrometry apparatus having the configuration described above. Therefore, the method of the present invention enables surface enhanced Raman spectrometry to be simply executed even on opaque samples.

Note that the surface enhanced Raman spectrometry method of the present invention may impregnate liquid samples into a plurality of locations of a liquid permeable substance, individually irradiate the measuring light beam onto the plurality of locations, and detect Raman scattered light which is generated during each irradiation operation. In this case, Raman spectrometry can be efficiently executed for a plurality of components included in the liquid sample.

In addition, the surface enhanced Raman spectrometry method of the present invention may individually irradiate the measuring light beam onto a plurality of locations of a solid sample, and detect Raman scattered light which is generated during each irradiation operation. In this case, the distribution, represented by the concentration thereof, for example, of a specific component within the solid sample can be efficiently obtained.

BEST MODE FOR CARRYING OUT THE INVENTION

Figure 1:
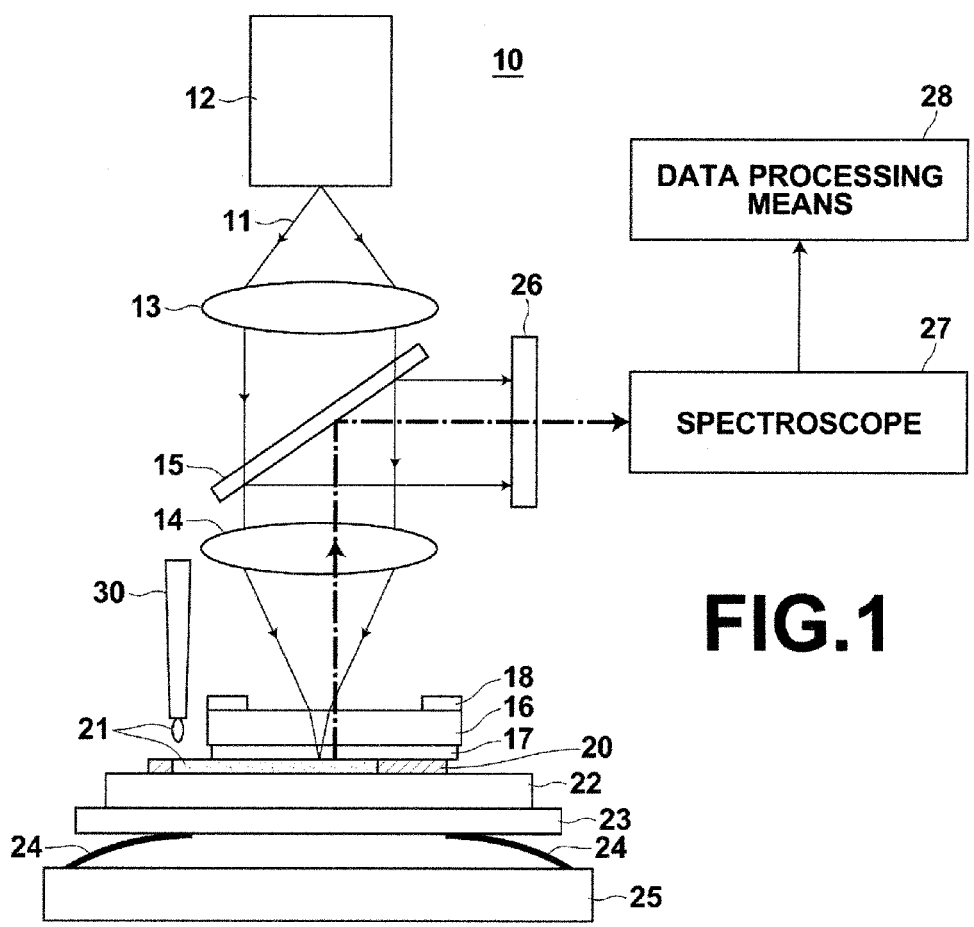
FIG. 1 is a schematic side view that illustrates a surface enhanced Raman spectrometry apparatus according to an embodiment of the present invention.

Hereinafter, an embodiment of the present invention will be described in detail with reference to the attached drawings. FIG. 1 is a schematic side view that illustrates a surface enhanced Raman spectrometry apparatus 10 according to an embodiment of the present invention. As illustrated in FIG. 1, the surface enhanced Raman spectrometry apparatus 10 includes: a light source 12 such as a semiconductor laser that emits a measuring light beam 11; a collimating lens 13 that collimates the measuring light beam 11 which is emitted from the light source 12 as light in a divergent state; a focusing lens 14 that causes the collimated measuring light beam 11 to converge on a measurement surface to be described later; a beam splitter 15 provided between the focusing lens 14 and the collimating lens 13; a transparent substrate 16 formed by optical glass, for example, and a metal layer 17 having a fine structure of protrusions and recesses, formed on a surface of the transparent substrate 16, that is, the lower surface of the transparent substrate 16 in FIG. 1.

In addition, the surface enhanced Raman spectrometry apparatus 10 includes: a positioning member 18 that abuts the upper surface of the transparent substrate 16 and regulates the upper position of the transparent substrate 16; a glass substrate 22 provided under the transparent substrate 16 to hold a piece of filter paper 20 between itself and the metal layer 17; a substrate holding plate on which the glass substrate 22 is placed and fixed; and a base 25 provided under the substrate holding plate 23 via a plurality of plate springs 24.

Further, the surface enhanced Raman spectrometry apparatus 10 includes: a measuring light beam cutoff filter 26 provided at the side of the beam splitter 15; a spectroscope 27 for spectrally detecting Raman scattered light to be described later, which passes through the measuring light beam cutoff filter 26; and a data processing means 28 constituted by a computer system, for example, for processing the output of the spectroscope 27.

Figure 5:
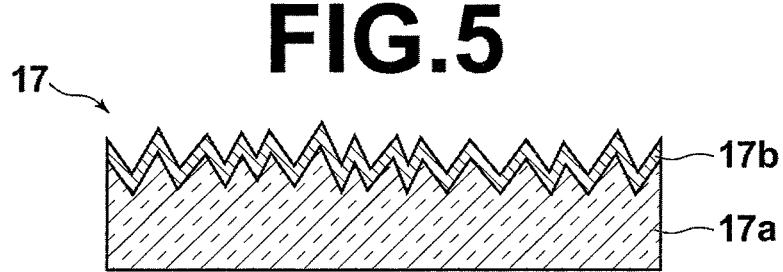
FIG. 5 is side view of the metal layer 17.

FIG. 5 shows a side view of the metal layer 17. The metal layer 17 may be formed by a three step process. Such a three step process includes: a thin film forming step, in which a thin film formed by a first metal or a first metal oxide is formed on the transparent substrate; a structure layer of fine protrusions and recesses producing step, in which a structure layer 17a of fine protrusions and recesses formed by a hydroxide of the first metal or the first metal oxide is produced by causing the thin film to undergo a hydrothermal reaction; and a metal layer producing step, in which a metal structure layer 17b of fine protrusions and recesses formed by the second metal is produced on the surface of the structure layer 17a of fine protrusions and recesses.

Note that it is preferable for the second metal to be: gold (Au), silver (Ag), copper (Cu), aluminum (Al), platinum (Pt), and alloys having these metals as their main components. Au and Ag are particularly preferable. In addition, the metal vapor deposition method, for example, may be employed in the metal layer producing step that produces the metal layer formed by the second metal. In the case that the vapor deposition method is applied and gold is employed as the second metal, it is desirable for the vapor deposited film thickness to be 30 nm or greater. Alternatively, in the case that the vapor deposition method is applied and silver is employed as the second metal, it is desirable for the vapor deposited film thickness to be 150 nm or less.

As a further alternative, a fine metal particle dispersing step, in which fine metal particles formed by the second metal are dispersed on the surface of the structure layer 17a of fine protrusions and recesses, may be applied as the metal layer producing step. In this case, it is preferable for fine metal particles having diameters of 100 nm or less to be employed.

Aluminum (Al) may be employed as the first metal, and alumina ($Al_2O_3$) may be employed as the first metal oxide.

Meanwhile, it is desirable for the hydroxide to be at least one of Bayerite and Boehmite.

Further, the metal layer 17 is not limited to that formed by the steps described above, and may be a metal layer, the surface of which has undergone a roughening process. An electrochemical process that utilizes oxidation reduction or the like may be employed as the roughening process.

Further, the metal layer 17 may be that having other known structures. For example, "Nanosphere arrays with controlled sub-10-nm gaps as surface-enhanced raman spectroscopy substrates", J. AM. CHEM. SOC. Vol. 127, pp. 14992-14993, 2005 discloses a metal layer having a plurality of Au particles, the surfaces of which have been modified with CTAB (cetyltrimethylammonium bromide) are arranged on an ITO substrate. As another example, Japanese Unexamined Patent Publication No. 2005-233637 discloses a metal layer in which a thin film formed by gold nanorods is provided on a substrate. Such metal layers may be employed in the present invention as appropriate.

Figure 2:
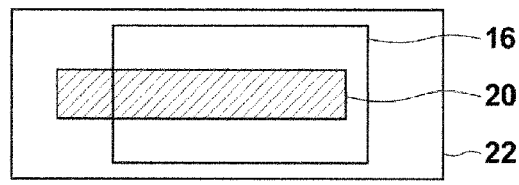
FIG. 2 is a plan view that illustrates a portion of the apparatus of FIG. 1.

Hereinafter, the operation of the surface enhanced Raman spectrometry apparatus 10 will be described. During Raman spectrometry, first, the glass substrate 22 and the substrate holding plate 23 are pressed downward against the pressing force of the plate springs 24, and a piece of filter paper 20 is placed on the glass substrate 22. At this time, the filter paper 20 is placed such that one end thereof protrudes outward from the side edge of the transparent substrate 16, as illustrated in FIG. 2. When the downward pressing force applied on the glass substrate 22 and the substrate holding plate 23 is released in this state, the filter paper 20 is held in a sandwiched state between the metal layer 17 on the surface of the transparent substrate 16 and the glass substrate 22.

Note that the upper surface of the transparent substrate 16 abuts the positioning member 18 at this time. Therefore, the transparent substrate 16 is maintained at a predetermined position in the vertical direction against the pressing force of the plate springs 24. The filter paper 20 is set at a predetermined position in the vertical direction in this manner.

After the filter paper 20 is set as described above, a liquid sample 21 is dripped onto the protruding end of the filter paper 20 by a dripping means 30 such as a pipette. The dripped liquid sample 21 permeates substantially the entire length of the filter paper 20. Note that the liquid sample 21 may be dripped onto the filter paper 20 after the filter, paper 20 is set, or the liquid sample 21 may permeate the filter paper 20 first, and then the filter paper 20 may be set.

After the liquid sample 21 is caused to permeate into the filter paper 20, the light source 12 is turned ON. The measuring light beam 11 such as a laser beam emitted by the light source 12 is irradiated through the transparent surface 16 such that it becomes converged at the surface of the filter paper 20 (the surface which is in contact with the metal layer 17), which is a measurement surface. Raman scattered light is generated at the filter paper 20 due to irradiation of the measuring light beam 11. The Raman scattered light passes through the transparent substrate 16, is focused by the focusing lens 14, is reflected by the beam splitter 15, passes through the measuring light beam cutoff filter 26, and enters the spectroscope 27, as indicated by the dotted line in FIG. 1.

The Raman scattered light has a wavelength different from that of the measuring light beam 11. The difference in energy, that is, the difference in wavelengths, between the Raman scattered light and the measuring light beam corresponds to the molecular structure or the crystal structure of an analysis target substance included in the liquid sample 21. The spectroscope 27 spectrally detects the Raman scattered light, and outputs the detection results to the data processing means 28.

The data processing means identifies the analysis target substance included in the liquid sample 21, based on the input spectral detection results.

In the present apparatus, the measuring light beam 11 is irradiated onto the filter paper 20 in a state in which the filter paper impregnated with the liquid sample is in contact with the metal layer 17. Therefore, the Raman scattered light can be significantly amplified then detected.

A notch filter or a short wavelength cutoff filter that transmits the Raman scattered light but cuts off the measuring light beam 11 reflected by the measurement surface may be employed as the measuring light beam cutoff filter 26.

As is clear from the description above, the light detecting means that spectrally detects Raman scattered light is constituted by the beam splitter 15, the measuring light beam cutoff filter 26, and the spectroscope 27 in the present embodiment.

As described above, the surface enhanced Raman spectrometry apparatus 10 of the present embodiment irradiates the measuring light beam 11 onto the filter paper 20 through the transparent substrate 16 while holding the filter paper 20 impregnated with the liquid sample 21 between the transparent substrate 16 and the glass substrate 22, and spectrally detects Raman scattered light through the transparent substrate 16. Here, the Raman scattered light is not cut off by the filter paper 20 even if the filter paper 20, which is a sample, is opaque. Therefore, Raman spectrometry of the liquid sample 21 can be performed in a simple manner.

In addition, the transparent substrate 16 abuts the positioning member 18 and the position thereof in the vertical direction, that is, the position of the filter paper 20 in the vertical direction, is maintained at a predetermined position. Therefore, the position of the measurement surface at which the measuring light beam 11 is converged, that is, the position of the upper surface of the filter paper 20 is positively maintained at the predetermined position, even if the filter paper 20 swells by being impregnated by the liquid sample 21.

In addition, the surface enhanced Raman spectrometry 10 of the present embodiment can be favorably employed to perform measurements on liquid samples separated from each other by chromatography, and particularly paper chromatography. This point will be described with reference to FIGS. 3 and 4. Note that in FIGS. 3 and 4, elements which are the same as those illustrated in FIGS. 1 and 2 are denoted with the same reference numerals, and detailed descriptions thereof will be omitted insofar as they are not particularly necessary.

Figure 3:
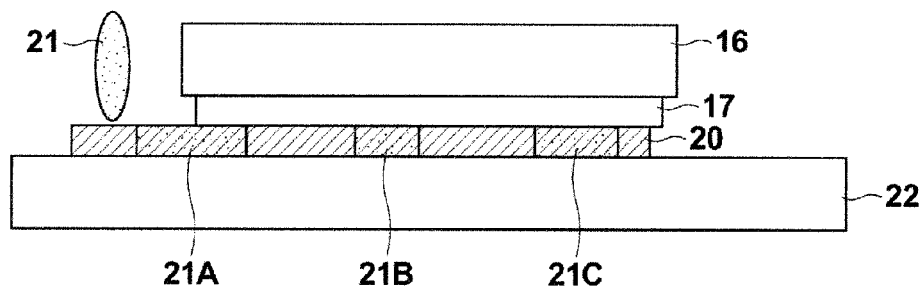
FIG. 3 is a side view for explaining a step of a Raman spectrometry operation performed employing the apparatus of FIG. 1.
Figure 4:
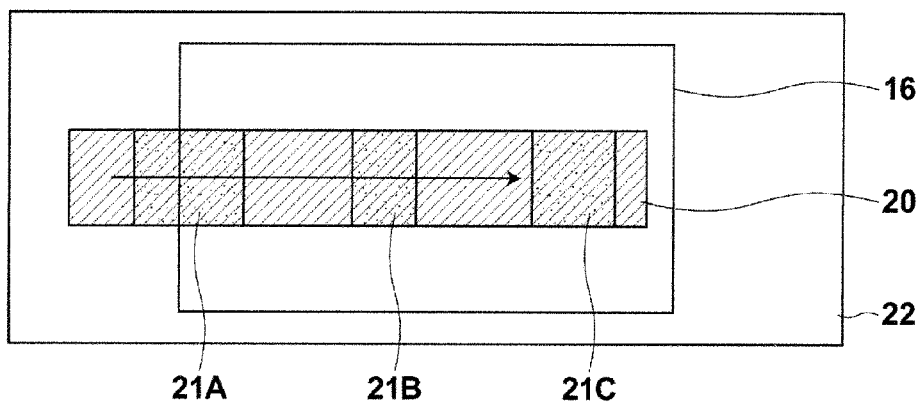
FIG. 4 is a plan view for explaining a step of a Raman spectrometry operation performed employing the apparatus of FIG. 1.

FIGS. 3 and 4 are a side view and a plan view of a piece of filter paper 20 impregnated with liquid samples 21A, 21B, and 21C which are separated from each other, respectively. As illustrated in FIG. 3, when a liquid sample 21 is dripped onto the end portion of the filter paper 20, the liquid sample 21 is separated according to the different components included therein, and held by the filter paper 20 as illustrated by reference numerals 21A, 21B, and 21C.

The measuring light beam 11 may be individually irradiated onto the plurality of locations of the filter paper 20 at which the liquid samples 21A, 21B, and 21C are held, and Raman scattered light which is generated during each irradiation operation may be detected by the configuration illustrated in FIG. 1. In this case, Raman spectrometry can be efficiently executed for a plurality of components included in the liquid sample.

Note that the measuring light beam irradiating optical system may be moved along the length direction of the filter paper 20 or the measuring light beam irradiating optical system may be fixed and the mechanism that holds the filter paper 20 may be moved, for example, in order to individually irradiate the measuring light beam 11 onto the plurality of locations of the filter paper 20 as described above.

An embodiment in which the filter paper 20 impregnated with the liquid sample 21 was employed as a sample has been described above. However, the surface enhanced Raman spectrometry method of the present invention is not limited to such a configuration. The surface enhanced Raman spectrometry method of the present invention can also be applied to a case in which a solid sample, such as a slice of living tissue, itself is employed as a sample. In such a case, the solid sample may be placed in the configuration of FIG. 1 instead of the filter paper 20.

In such a case, the measuring light beam may be individually irradiated onto a plurality of locations of the solid sample, and Raman scattered light which is generated during each irradiation operation may be detected. In this case, the distribution, represented by the concentration thereof, for example, of a specific component within the solid sample can be efficiently obtained.

What is claimed is:

1. A surface enhanced Raman spectrometry apparatus, comprising:
    a transparent substrate;
    a metal member that causes surface enhanced Raman scattering to occur, formed on a surface of the transparent substrate;
    a pressing mechanism that presses a sample placed in contact with the metal member against the metal member;
    a measuring light irradiating optical system that irradiates a measuring light beam onto the sample through the transparent substrate; and
    a light detecting section that spectrally detects Raman scattered light, which is generated when the measuring light beam is irradiated onto the sample, through the transparent substrate;
    the metal member has a structure of protrusions and recesses in which the sizes of the protrusions and recesses is smaller than the wavelength of the measuring light beam; and
    the metal member being constituted by a structure layer having protrusions and recesses formed by boehmite and a metal layer formed on the structure layer having protrusions and recesses.

2. A surface enhanced Raman spectrometry apparatus as defined in claim 1, further comprising:
    a positioning member that maintains the transparent substrate at a predetermined position against a pressing force applied by the pressing mechanism.

3. A surface enhanced Raman spectrometry apparatus as defined in claim 1, wherein:
    the pressing mechanism comprises a plate shaped member that contacts the sample and a spring means for urging the plate shaped member toward the metal member.

4. A surface enhanced Raman spectrometry apparatus as defined in claim 1, wherein:
    the main component of the metal member is at least one metal selected from a group consisting of: Au, Ag, Cu, Al, Pt, Ni, Ti, and alloys thereof.

5. A surface enhanced Raman spectrometry method that performs Raman spectrometry using a surface enhanced Raman spectrometry apparatus as defined in claim 1.

6. A surface enhanced Raman spectrometry method as defined in claim 5, wherein:
    a liquid permeable substance impregnated with a liquid sample is employed as the sample.

7. A surface enhanced Raman spectrometry method as defined in claim 6, wherein:
    filter paper is employed as the liquid permeable substance.

8. A surface enhanced Raman spectrometry method as defined in claim 6, wherein:
    liquid samples are impregnated into each of a plurality of locations of the liquid permeable substance;
    the measuring light beam is individually irradiated on each of the plurality of locations; and
    Raman scattered light generated by each irradiating operation is detected.

9. A surface enhanced Raman spectrometry method as defined in claim 8, wherein:
    the liquid samples impregnated into each of the plurality of locations are separated from each other by chromatography.

10. A surface enhanced Raman spectrometry method as defined in claim 5, wherein:
    a solid sample itself is employed as the sample.

11. A surface enhanced Raman spectrometry method as defined in claim 10, wherein:
    the measuring light beam is individually irradiated on each of a plurality of locations of the solid sample; and
    Raman scattered light generated by each irradiating operation is detected.

* * * * *